(12) United States Patent
George et al.

(10) Patent No.: US 9,907,808 B2
(45) Date of Patent: Mar. 6, 2018

(54) METHOD FOR RELIEVING NEUROGENIC PAIN

(71) Applicant: Nova Neura, LLC, Phoenix, AZ (US)

(72) Inventors: David George, Scottsdale, AZ (US); Stuart Fife, Savannah, GA (US); Howard Rosen, Huntington Beach, CA (US)

(73) Assignee: Nova Neura, LLC, Phoenix, AZ (US)

( * ) Notice: Subject to any disclaimer, the term of this patent is extended or adjusted under 35 U.S.C. 154(b) by 0 days.

(21) Appl. No.: 15/697,324

(22) Filed: Sep. 6, 2017

(65) Prior Publication Data

US 2017/0360814 A1    Dec. 21, 2017

Related U.S. Application Data

(63) Continuation of application No. 14/612,006, filed on Feb. 2, 2015, now Pat. No. 9,757,401, which is a continuation of application No. 14/294,034, filed on Jun. 2, 2014, now abandoned, which is a continuation of application No. 13/479,998, filed on May 24, 2012, now abandoned, which is a continuation of application No. 13/417,053, filed on Mar. 9, 2012, now abandoned, which is a continuation of application No. 13/295,010, filed on Nov. 11, 2011, now abandoned.

(51) Int. Cl.
| | |
|---|---|
| *A61K 31/7004* | (2006.01) |
| *A61K 36/886* | (2006.01) |
| *A61K 31/047* | (2006.01) |
| *A61K 47/02* | (2006.01) |
| *A61K 9/00* | (2006.01) |
| *A61K 9/06* | (2006.01) |
| *A61K 9/08* | (2006.01) |

(52) U.S. Cl.
CPC ........ *A61K 31/7004* (2013.01); *A61K 9/0014* (2013.01); *A61K 31/047* (2013.01); *A61K 36/886* (2013.01); *A61K 47/02* (2013.01); *A61K 9/06* (2013.01); *A61K 9/08* (2013.01)

(58) Field of Classification Search
None
See application file for complete search history.

(56) References Cited

U.S. PATENT DOCUMENTS

| | | |
|---|---|---|
| 5,383,324 A | 1/1995 | Segers et al. |
| 5,420,114 A | 5/1995 | Clodman et al. |
| 7,625,586 B2 | 12/2009 | Burgess |
| 8,598,207 B2 | 12/2013 | Buehler |
| 9,757,401 B2 | 9/2017 | Rosen |
| 2001/0051166 A1 | 12/2001 | Luo et al. |
| 2003/0175328 A1 | 9/2003 | Shefer et al. |
| 2003/0175333 A1 | 9/2003 | Shefer et al. |
| 2008/0146672 A1 * | 6/2008 | Denton ................ A61K 9/0014 514/626 |
| 2012/0034320 A1 | 2/2012 | Murray et al. |
| 2012/0121721 A1 | 5/2012 | James |
| 2012/0230968 A1 | 9/2012 | Worden, Sr. |
| 2013/0122116 A1 | 5/2013 | Rosen |
| 2013/0236530 A1 | 9/2013 | Rosen |
| 2013/0236577 A1 | 9/2013 | Rosen |
| 2014/0271828 A1 | 9/2014 | Rosen |

OTHER PUBLICATIONS

Gatej et al. Role of the pH on Hyaluronan Behavior in Aqueous Solution. Biomolecules 2005, 6, 61-67.
PCCA. PCCA Lipoderm®. Website, http://www.ppcarx.com, originally downloaded Dec. 24, 2014, 1 page.
Rosenthal et al. Experiments on Histamine as the Chemical Mediator for Cutaneous Pain. Abbott Lab., 1939.
Turan et al. The prevention of pain from injection of rocuronium by magnesium sulphate, lignocaine, sodium bicarbonate and alfentanil. Anaeth Intensive Care, 2003;31(3):277-81.

* cited by examiner

*Primary Examiner* — Isis A Ghali
(74) *Attorney, Agent, or Firm* — Craig R. Miles; CR MILES P.C.

(57) ABSTRACT

An inventive composition including an amount of sugar or sugar alcohol, an amount of alkalizing agent, and an amount of vehicle; whereby the inventive composition is formulated for transdermal administration to alleviate one or more disorder symptoms, for example neurogenic pain, or to treat one or more disorders, for example neurogenic inflammation.

13 Claims, No Drawings

METHOD FOR RELIEVING NEUROGENIC PAIN

This United States Patent Application is a continuation of U.S. patent application Ser. No. 14/612,006, filed Feb. 2, 2015, now U.S. Pat. No. 9,757,401, issued Sep. 12, 2017, which is a continuation-in-part of U.S. patent application Ser. No. 14/294,034, filed Jun. 2, 2014, which is a continuation of U.S. patent application Ser. No. 13/479,998, filed May 24, 2012, which is a continuation-in-part of U.S. patent application Ser. No. 13/417,053, filed Mar. 9, 2012, which is a continuation-in-part of U.S. patent application Ser. No. 13/295,010, filed Nov. 11, 2011, each hereby incorporated by reference herein.

I. BACKGROUND OF THE INVENTION

Pain is one of the most frequent symptoms for which patients seek medical intervention. Pain may be classified as acute or chronic. Acute pain may be generally associated with excessive noxious stimulus resulting in a severe distressful sensation whereas chronic pain may be associated with physiological changes resulting from tissue or nerve injury leading to hyperalgesia, an increased amount of pain associated with a mild noxious stimulus, or allodynia, a pain induced by a non-noxious stimulus.

Neurogenic pain is a neurological disorder caused by insult to peripheral nerves, resulting in chronic pain and varying combinations of sensory symptoms, including paresthesia, loss of sensation, and even motor weakness. Neurogenic pain may be long-lasting, and may develop days or month following the injury. Often, this type of chronic pain may be observed in diseases affecting the peripheral nervous system, such as nerve compression syndromes, cutaneous sensory neuropathies and polyneuropathies (of which diabetic neuropathy may be the most well-known).

Amongst the various types of chronic pain, understanding and management of neurogenic pain remains a considerably challenging task for researchers and clinicians. Despite the rapid development of neuroscience and the discovery of new pharmaceutical compounds, a need continues to exist for an effective treatment based on a basic understanding of the contributing molecular mechanisms of neurogenic pain.

Neurogenic pain involves alterations in the function of both the peripheral and central nervous system, postulated to be caused by changes in mechano-insensitive peptidergic nociceptors referred to as "silent" or "sleeping" nociceptors, which are chemo-sensitive and respond to noxious chemicals typically released in response to tissue or nerve trauma. Once sensitized, the phenotype of the nociceptors can be altered, whereby the formerly "silent" or "sleeping" nociceptors become "polymodal" or "awake" nociceptors (C fibers), which release significant amounts of pro-inflammatory neuropeptides, such as calcitonin gene-related peptide (CGRP) or substance P (SP), initiating neurogenic inflammation in combination with enhancing action potentials, thereby resulting in increased nociception.

Following nerve injury, increased excitability and sensitivity is observed in the cell body of the injured dorsal root ganglia neurons and neighboring intact afferent neurons. This enhanced stimulation involving the primary afferent neurons is defined as peripheral sensitization, which is mediated by increased expression of the transient receptor potential (TRP) family of non-specific cation channels, including transient receptor potential cation channel subfamily V member 1 (TRPV1), which is expressed in C fibers and Aδ fibers. Another mechanism leading to peripheral sensitization includes the accumulation of voltage-gated sodium channels at the site of the injured nerve and at the dorsal root ganglion, resulting in abnormal ectopic excitability of afferent neurons. These changes may be perceived as spontaneous positive sensations, such as paresthesia (a sensation of tingling, burning, pricking, or numbness of skin) or dysthesia (an unpleasant, abnormal sense of touch).

Central sensitization, defined as the activation of second order nociceptive neurons in the dorsal horn of the spinal cord by peripheral nerve damage, results from the release of glutamate, SP, or other transmitters or cytokines, such as adenosine-5'-triphosphate (ATP), chemokine (C—C motif) ligand 2 (CCL2), or interferon gamma (INFγ), from the central terminals of primary nociceptive afferents in the dorsal horn. The overall effect of these changes may be prolonged excitability of the spinal cord neurons (long-term potentiation).

Further contributing factors to the development of neurogenic pain include the involvement of spinal cord microglia and astrocytes in enhancing pain, whereby ATP-activated microglial P2X4 and P2X7 receptors stimulate the p38 mitogen-activated protein kinases (p38– MAPK) signalling cascade, resulting in release of substances such as brain-derived neurotrophic factor (BNDF), down-regulation of potassium/chloride cotransporters, and diminished inhibitory neurotransmission (GABAergic inhibition).

Additionally, following an injury, various inflammatory substances such as histamines, prostaglandins, or cytokines, may be released from inflammatory cells which have migrated through the blood to the site of the injured tissue. When the injury results in nerve damage, the peripheral terminals of sensory neurons may be activated, resulting in inflammation characterized by the release of neuropeptides, such as CGRP, SP, or calcitonin, from the C fiber terminal, which can lead to vasodilation, edema, or pain. As such, neurogenic inflammation plays an integral role in the pathophysiology of neurogenic pain.

Successful treatment of neurogenic pain requires direct targeting of the receptors and transmitters involved. Conventional therapeutic strategies aim to reduce neuron excitability through alterations in ion channel activity, which may be targeted by compounds such as gabapentin or lidocaine, or modulate central neurotransmission, which may be targeted by compounds such as opioids or tricyclic antidepressants. Despite consistent efficacy observed in randomized trials and meta-analyses, the use of these agents may be limited due to debilitating side effects, such as sedation, somnolence, dry mouth, urinary retention, erythema, ataxia, or the like, or combinations thereof. Moreover, patients using these compounds must be closely monitored and dose tapering may be required to prevent withdrawal symptoms. Accordingly, a need exists for a novel alternative characterized by maximal therapeutic efficacy, minimal toxicity, and low incidence of side effects.

II. SUMMARY OF THE INVENTION

A broad object of a particular embodiment of the invention can be to provide an inventive composition including an amount of sugar or sugar alcohol, an amount of alkalizing agent, and an amount of vehicle; whereby the inventive composition is formulated for transdermal administration.

Another broad object of a particular embodiment of the invention can be to provide a method of using the inventive composition, the method including transdermally administering the inventive composition to alleviate one or more disorder symptoms, for example neurogenic pain, or to treat one or more disorders, for example neurogenic inflammation.

Another broad object of a particular embodiment of the invention can be to provide a method of producing an inventive composition, the method including combining an amount of sugar or sugar alcohol, an amount of alkalizing agent, and an amount of vehicle; and formulating the inventive composition for transdermal administration.

Naturally, further objects of the invention are disclosed throughout other areas of the specification, drawings, and claims.

III. DETAILED DESCRIPTION OF THE INVENTION

A method of using a particular embodiment of the inventive composition including an amount of sugar or sugar alcohol, an amount of alkalizing agent, and an amount of vehicle, whereby the inventive composition is formulated for transdermal administration, can include administering the inventive composition to an external surface of a body to alleviate one or more disorder symptoms, for example neurogenic pain, or to treat one or more disorders, for example neurogenic inflammation.

The term "sugar" for the purposes of this invention means any carbohydrate or saccharide, including monosaccharides, disaccharides, oligosaccharides, or polysaccharides.

The term "sugar alcohol" for the purposes of this invention means any polyol (or polyhydric alcohol) derived from a sugar. The polyol can typically include an alcohol group ($CH_2OH$) in place of an aldehyde group (CHO) of the parent sugar.

The term "alkalizing agent" for the purposes of this invention means an agent capable of adjusting a pH from a lesser alkalinity toward a greater alkalinity.

The term "symptom" for the purposes of this invention means any discomfort or combination of discomforts associated with a disorder. Without limiting the breadth of the foregoing, symptoms can include: pain, dyesthesia, paresthesia, sensory loss, allodynia, hyperpathia, reduced range-of-motion, motor weakness, or the like, or combinations thereof.

The term "disorder" for the purposes of this invention means a physical or mental condition which may not be normal or healthy. Without limiting the breadth of the foregoing, a disorder can include: known compressive mononeuropathies (such as carpal tunnel syndrome, cubital tunnel syndrome, or tarsal tunnel syndrome), regional pain conditions (such as sub-occipital neuralgia, facial neuralgias, headache, neck pain, or back pain), acute joint injury which may include a component of nerve inflammation (such as ankle sprain or strain), tendinopathies potentially promoted or aggravated by concomitant neurogenic components (such as Achilles tendonosis, lateral epicondylosis, or medial epicondylosis), or isolated inflammation of any one or more peripheral nerves (such as cranial and upper cervical nerve branch derivatives of the face and cranium).

The term "topical administration or "transdermal administration" for the purposes of this invention means the administration of one or more components of a composition or compound to and typically, but not necessarily, through the epidermis on any external surface of a body. As to particular embodiments, topical administration or transdermal administration can mean the administration of one or more components of a composition or compound to the epidermis on any external surface of a body and typically, but not necessarily, through the dermis. Following topical administration or transdermal administration, one or more components of the composition or compound may or may not be systemically bioavailable.

Where trade names or trademarks are utilized herein, whether in Table 1 through Table 7, or any table, figure, or portion of the description, the trade name material or the trademark material is understood to have the chemicals or ingredients in the amounts or combinations as described below. The trade name material or trademark material or a substantially equivalent product or combination of chemicals or ingredients can be utilized in embodiments of the inventive composition. It is further understood that where a trade name material or trademark material is utilized in a table or figure that substantially equivalent chemicals or ingredients in the amounts and combinations as indicated below can be utilized in substitution of the trade name material or trademark material. A person of ordinary skill in the art can convert the weight percentages shown in the tables or figures to determine the amount of each chemical or ingredient to mix when the equivalent of the trade name material or trademark material is prepared.

Where the constituents of a particular trade name material or trademark material have been set out a first time in the description below, each applies to the subsequent uses of the trade name material or trademark material in the description, tables and figures.

Now referring primarily to Table 1, embodiments of the inventive composition can include formulations having raw materials admixed in the exemplary weight percentages ("Weight Percent") shown in column two of Table 1. Numerous embodiments of the inventive composition can be prepared by altering the weight percentages of the raw materials within the range weight percentages ("Range Weight Percent") shown in column three of Table 1 with an amount of vehicle making up the balance.

TABLE 1

| Raw Material | Weight Percent | Range Weight Percent |
|---|---|---|
| Sugar or Sugar Alcohol | 20 | 2 to 30 |
| Alkalizing Agent | 5 | 0.1 to 15 |
| Vehicle | 75 | 55 to 97.9 |

As to particular embodiments, the sugar can include a monosaccharide, such as ribose (CAS No: 50-69-1), xylose (CAS No: 58-86-6), fructose (CAS No: 57-48-7), dextrose (glucose) (CAS No: 50-99-7), galactose (CAS No: 59-23-4), mannose (CAS No: 31103-86-3), sorbose (CAS No: 87-79-6), or the like, or combinations thereof, all of which can be obtained from Sigma-Aldrich, 3050 Spruce Street, St. Louis, Mo., USA. As to other particular embodiments, the sugar can include a disaccharide, such as sucrose (CAS No: 57-50-1), maltose (CAS No: 69-79-4), lactose (CAS No: 63-42-3), lactulose (CAS No: 4618-18-2), trehalose (CAS No: 99-20-7), cellobiose (CAS No: 528-50-7), or the like, or combinations thereof, all of which can be obtained from Sigma-Aldrich, 3050 Spruce Street, St. Louis, Mo., USA.

The sugar can be generally included in an amount of about 2% to about 30% by weight of the inventive composition; however, greater or lesser weight percents of the sugar can be included depending on the disorder symptom to be alleviated or the disorder to be treated.

As to particular embodiments, the amount of sugar included in the inventive composition can be selected from the group including or consisting of: between about 5% to about 30% by weight of the inventive composition; between about 10% to about 30% by weight of the inventive composition; between about 15% to about 30% by weight of the inventive composition; and between about 20% to about 30% by weight of the inventive composition. As to the particular embodiment of the inventive composition shown in Table 1, the amount of sugar, for example dextrose, included can be about 20% by weight of the inventive composition.

The amount of sugar included in the inventive composition can be influenced by factors such as user anatomy, physiology, or biochemistry of the epidermis or underlying tissue; disorder symptom targeted for alleviation; disorder targeted for treatment; observable effect(s) of the application of the inventive composition; or the like; or combinations thereof; but not so much as to cause discomfort to the user or irritation to the epidermis or underlying tissue.

The sugar alcohol can include a polyol derived from a monosaccharide or a disaccharide, including glycerol (CAS No: 56-81-5), erythritol (CAS No: 10030-58-7), threitol (CAS No: 2418-52-2), arabitol (CAS No: 7643-75-6), xylitol (CAS No: 87-99-0), adonitol (CAS No: 488-81-3), mannitol (CAS No: 69-65-8), sorbitol (CAS No: 50-70-4), dulcitol (CAS No: 608-66-2), fucitol (CAS No: 13074-06-1), iditol (CAS No: 488-45-9), inositol (CAS No: 87-89-8), volemitol (CAS No: 30635-52-0), isomalt (CAS No: 64519-82-0), maltitol (CAS No: 585-88-6), lactitol (CAS No: 585-86-4), maltotriitol (CAS No: 32860-62-1), or the like, or combinations thereof, all of which can be obtained from Sigma-Aldrich, 3050 Spruce Street, St. Louis, Mo., USA.

The sugar alcohol can be generally included in an amount of about 2% to about 30% by weight of the inventive composition; however, greater or lesser weight percents of the sugar alcohol can be included depending on the disorder symptom to be alleviated or the disorder to be treated.

As to particular embodiments, the amount of sugar alcohol included in the inventive composition can be selected from the group including or consisting of: between about 5% to about 30% by weight of the inventive composition; between about 10% to about 30% by weight of the inventive composition; between about 15% to about 30% by weight of the inventive composition; and between about 20% to about 30% by weight of the inventive composition. As to the particular embodiment of the inventive composition shown in Table 1, the amount of sugar alcohol, for example mannitol, included can be about 20% by weight of the inventive composition.

The amount of sugar alcohol included in the inventive composition can be influenced by factors such as user anatomy, physiology, or biochemistry of the epidermis or underlying tissue; disorder symptom targeted for alleviation; disorder targeted for treatment; observable effect(s) of the application of the inventive composition; or the like; or combinations thereof; but not so much as to cause discomfort to the user or irritation to the epidermis or underlying tissue.

The alkalizing agent can include any agent capable of adjusting a pH from a lesser alkalinity toward a greater alkalinity, such as sodium bicarbonate (CAS No: 144-55-8), potassium citrate (CAS No: 866-84-2), calcium carbonate (CAS No: 471-34-1), calcium acetate (CAS No: 62-54-4), or the like, or combinations thereof, all of which can be obtained from Sigma-Aldrich, 3050 Spruce Street, St. Louis, Mo., USA.

As to particular embodiments, the alkalizing agent can include a salt. As to particular embodiments, the salt can include a monovalent cation, a divalent cation, or a trivalent cation, including but not limited to sodium, calcium, potassium, zinc, iron, magnesium, or the like, or combinations thereof. As to other particular embodiments, the salt can include an anion, including but not limited to chloride, acetate, ascorbate, bicarbonate, citrate, formate, fumarate, phosphate, succinate, borate, gluconate, lactate, malate, trimalate, panthothenate, thiocyanate, glycinate, sulphate, or the like, or combinations thereof.

As to particular embodiments, the salt can be selected from the group including or consisting of: sodium chloride, sodium acetate, sodium bicarbonate, sodium citrate, sodium phosphate, sodium dihydrogen phosphate, sodium hydrogen phosphate, sodium succinate, sodium borate, sodium gluconate, sodium citrate, sodium lactate, calcium citrate, calcium chloride, calcium pantothenate, calcium gluconate, calcium phosphate, potassium chloride, monopotassium phosphate, dipotassium phosphate, tripotassium phosphate, potassium gluconate, magnesium sulphate, magnesium chloride magnesium gluconate, magnesium acetate, magnesium malate, magnesium glycinate, magnesium lactate, zinc chloride, zinc sulphate and zinc acetate. Other exemplary salts may be formed from any combination of anions and cations listed above and may include, anhydrous, hydrates, dehydrates, or the like, or combinations thereof.

The alkalizing agent can be generally included in an amount of about 0.1% to about 15% by weight of the inventive composition; however, greater or lesser weight percents of the alkalizing agent can be included depending on the disorder symptom to be alleviated or the disorder to be treated. As to particular embodiments, the amount of alkalizing agent included in the inventive composition can be in a range of between about 6.5% to about 15% by weight of the inventive composition.

As to particular embodiments, the amount of alkalizing agent included in the inventive composition can be selected from the group including or consisting of: between about 1% to about 15% by weight of the inventive composition, between about 1% to about 15% by weight of the inventive composition, between about 2.5% to about 15% by weight of the inventive composition, between about 5% to about 15% by weight of the inventive composition, between about 7.5% to about 15% by weight of the inventive composition, between about 10% to about 15% by weight of the inventive composition, and between about 12.5% to about 15% by weight of the inventive composition. As to the particular embodiment of the inventive composition shown in Table 1, the amount of alkalizing agent, for example sodium bicarbonate, included can be about 5% by weight of the inventive composition.

The amount of alkalizing agent included in the inventive composition can be influenced by factors such as user anatomy, physiology, or biochemistry of the epidermis or underlying tissue; disorder symptom targeted for alleviation; disorder targeted for treatment; observable effect(s) of the application of the inventive composition; or the like; or combinations thereof; but not so much as to cause discomfort to the user or irritation to the epidermis or underlying tissue.

The vehicle can include one or more excipients in which the sugar or sugar alcohol can be solubilized or suspended. As to particular embodiments, the excipient can render the inventive composition suitable for topical application or transdermal application, whereby the vehicle can facilitate the transdermal administration of a portion of the amount of sugar or sugar alcohol and a portion of the amount of alkalizing agent. As illustrative examples, the inventive composition including the amount of sugar or sugar alcohol, amount of alkalizing agent, and the amount of vehicle can take the form of lotion, cream, emulsion, ointment, gel, foam, paste, oil, lipid delivery system, spray, drops, or the like, or combinations thereof.

The amount of vehicle included in the inventive composition can be influenced by factors such as user anatomy, physiology, or biochemistry of the epidermis or underlying tissue; disorder symptom targeted for alleviation; disorder targeted for treatment; observable effect(s) of the application of the inventive composition; or the like; or combinations thereof; but not so much as to cause discomfort to the user or irritation to the epidermis or underlying tissue.

As to particular embodiments, the vehicle can include an emulsion base, which can have an oil phase. As illustrative examples, the oil phase can include vegetable oils, animal oils, mineral oils, silicone oils, synthetic oils, fatty acids, fatty alcohols, phospholipids, paraffin waxes, or the like, or combinations thereof.

As to particular embodiments, the vehicle can further include one or more solubilizing agents, such as cyclodextrins, surfactants, organic solvents, alcohols, polysorbates, or the like, or combinations thereof.

As to particular embodiments, the vehicle can further include one or more viscosity-increasing agents, such as microcrystalline cellulose, carboxymethylcellulose sodium, propylene glycol alginate, xanthan gum, polyacrylic acid, or the like, or combinations thereof.

As to particular embodiments, the vehicle can further include one or more emulsifying or co-emulsifying agents, such as non-ionic surfactants, polyethylene glycol esters, polyoxypropylene glycol ethers, sorbitan esters, ethoxylated sorbitan esters, poly esters, or the like, or combinations thereof.

As to particular embodiments, the vehicle can further include one or more emulsion stabilizing agents, such as abietic acid, hydrogenated lanolin alcohol, calcium myristate, hydroxyaluminium distearate, aluminum isostearate, aluminum stearate, 7, 8-didehydrocholesterol, aluminum magnesium hydroxide, stearic acid, lauryl alcohol, hydroxyethyl cellulose, or the like, or combinations thereof.

As to particular embodiments, the vehicle can further include one or more preservatives or preserving agents, such as sorbic acid, methyl paraben, propyl paraben, benzoic acid, sodium benzoate cetrimide, phenoxyethanol, chlorphenisin, methylchloroisothiazolinone, or the like, or combinations thereof.

As to particular embodiments, the vehicle can further include one or more penetration enhancers, such as alcohols, sulphoxides, azone, pyrrolidones, urea, disubstituted aminoacetates, glycols (for example, propylene glycol), surfactants, terpenes, terpenoids, fatty acids, esters, cyclodextrins, phospholipids, or the like, or combinations thereof.

As to particular embodiments, the vehicle can further include water (CAS No: 7732-18-5), which can be filtered, de-ionized, distilled, or water otherwise filtered or purified.

As an illustrative example, the vehicle can include Pentravan®, having fatty acid alcohols, acids, esters, phospholipids, antioxidants, skin-feel enhancer, natural humectant, natural preservatives, nonionic emulsifiers, anionic emulsifiers, and buffer, which can be obtained from Fagron, 2400 Pilot Knob Road, St Paul, Minn. 55120, USA.

As an additional illustrative example, the vehicle can include Versatile®, having waters, fatty acid esters, alcohols, paraffinic silicone replacement, glidant, plant-derived emollient, vitamin E, nonionic emulsifiers, pro-liposomal phospholipids, and preservatives, which can be obtained from Fagron, 2400 Pilot Knob Road, St Paul, Minn. 55120, USA.

As yet an additional illustrative example, the vehicle can include VersaPro Cream Base™, which can be obtained from Medisca, 661 Route 3, Unit C, Plattsburgh, N.Y. 12901, USA.

As to particular embodiments, the inventive composition can further include an amount of magnesium. As to particular embodiments, the amount of magnesium can be provided by magnesium chloride, magnesium sulfate, or the like, or combinations thereof.

As to particular embodiments, the inventive composition can further include an amount of *Aesculus hippocastanum*. As to particular embodiments, the amount of *Aesculus hippocastanum* can be in a range of between about 0.25% to about 2% by weight of the inventive composition. As to particular embodiments, the amount of *Aesculus hippocastanum* can include an amount of aescin.

As to particular embodiments, the inventive composition can further include an amount of quercetin. As to particular embodiments, the amount of quercetin can be in a range of between about 0.1% to about 1% by weight of the inventive composition.

As to particular embodiments, the inventive composition can further include an amount of acetyl-L-carnitine. As to particular embodiments, the amount of acetyl-L-carnitine can be in a range of between about 0.025% to about 3% by weight of the inventive composition.

As to particular embodiments, the inventive composition can further include an amount of zinc. As to particular embodiments, the amount of zinc can be in a range of between about 0.025% to about 3% by weight of the inventive composition. As to particular embodiments, the amount of zinc can be provided by zinc oxide, zinc sulfate, or the like, or combinations thereof.

As to particular embodiments, the inventive composition can further include one or more colorants, fragrances, or the like, as persons of ordinary skill in the art would understand.

A method of using the inventive composition can include transdermally administering the inventive composition including an amount of sugar or sugar alcohol, an amount of alkalizing agent, and an amount of vehicle, whereby the inventive composition is formulated for transdermal administration.

As to particular embodiments, the method of using the inventive composition can further include transdermally administering the inventive composition to an external surface of a body to alleviate one or more disorder symptoms, for example to decrease neurogenic pain, or to treat one or more disorders, for example to decrease neurogenic inflammation.

As to particular embodiments, the method of using the inventive composition can further include transdermally administering the inventive composition along a nerve pathway of a nerve to decrease neurogenic pain or to decrease neurogenic inflammation of the nerve.

As to particular embodiments, transdermally administering the inventive composition can alkalize a perineural environment proximate the nerve by adjusting a pH of the perineural environment from a lesser alkalinity toward a greater alkalinity. As to particular embodiments, transdermally administering the inventive composition can decrease an amount of hydrogen ions (H+) in the perineural environment proximate the nerve.

Research suggests an association between tissue acidity and neurogenic inflammation whereby hydrogen ions (H+)

may prime the transient receptor potential cation channel subfamily V member (TrpV1), thereby increasing neurogenic inflammation and corresponding neurogenic pain. Accordingly, decreasing the amount of hydrogen ions (H+) by adjusting the perineural environment from a lesser alkalinity toward a greater alkalinity may be beneficial for alleviating neurogenic pain or treating neurogenic inflammation.

As to particular embodiments, transdermally administering the inventive composition can decrease a viscosity of hyaluronic acid (also known as hyaluronan, hyaluronate, or HA), which is an anionic, nonsulfated glycosaminoglycan widely distributed throughout connective, epithelial, and neural tissues. Particularly, hyaluronic acid can be found between fascial layers, acting as a lubricant to facilitate fascial glide. As peripheral nerves, especially superficial sensory nerves, can typically be enveloped between fascial layers, decreasing the viscosity of hyaluronic acid may decrease friction or mechanical irritation of the nerves by the fascia. Research suggests that adjusting the pH of a perineural environment from a lesser alkalinity toward a greater alkalinity may result in a conformational change in the hyaluronic acid molecule resulting from a degradation of attraction forces between hyaluronic acid molecules, thereby increasing the flexibility of the hyaluronic acid polymer and correspondingly decreasing the viscosity of hyaluronic acid.

As to particular embodiments, the method of using the inventive composition can further include transdermally administering the inventive composition formulated as a fluid, such as a lotion, cream, emulsion, ointment, gel, foam, paste, oil, lipid delivery system, spray, drops, or the like, or combinations thereof, to the external surface of the body to alleviate one or more disorder symptoms or to treat one or more disorders.

As to particular embodiments, the method of using the inventive composition can further include administering one or more physical skin penetration enhancement techniques before, during, or after transdermally administrating the inventive composition to the external surface of the body to alleviate one or more disorder symptoms or to treat one or more disorders. As illustrative examples, physical skin penetration enhancement techniques can include phonophoresis, sonophoresis, iontophoresis, electroporation, radiofrequency-driven skin microchanneling, microneedles, massage, occlusion, heating, cooling, or the like, or combinations thereof.

Now referring primarily to Table 2, which evidences the results of a method of transdermally administering a particular embodiment of the inventive composition to twenty-six subjects (indicated in column 1 as "Subject Number") who presented with various pain-related complaints (indicated in column 2 as "Primary Complaint"). As to this particular embodiment, the inventive composition included dextrose in an amount of about 20% by weight of the inventive composition, sodium bicarbonate in an amount of about 5% by weight of the inventive composition, and vehicle in an amount of about 75% by weight of the inventive composition.

TABLE 2

| Subject Number | Primary Complaint | Pre-Admin Pain Level | 5 Minutes Post-Admin Pain Level | Percent Reduction in Pain Level | 24 Hours Post-Admin Pain Level | Percent Reduction in Pain Level |
|---|---|---|---|---|---|---|
| 1 | Post-surgical knee pain | 4 | 0 | 100% | 1 | 75% |
| 2 | Idiopathic knee pain | 3 | 0 | 100% | 1 | 67% |
| 3 | Radiating leg pain | 4 | 0 | 100% | 1 | 75% |
| 4 | Post-surgical knee pain | 8 | 0 | 100% | 2 | 75% |
| 5 | Iliotibial band pain | 2 | 0 | 100% | 0 | 100% |
| 6 | Post-surgical hip pain | 3 | 0 | 100% | 0 | 100% |
| 7 | Elbow pain | 4 | 0 | 100% | 0 | 100% |
| 8 | Severe low back & leg pain | 8 | 0 | 100% | 1 | 88% |
| 9 | Neck pain & face paresthesia | 8 | 0 | 100% | 0 | 100% |
| 10 | Elbow/forearm pain | 4 | 0 | 100% | 1 | 75% |
| 11 | Shoulder pain | 4 | 0 | 100% | 1 | 75% |
| 12 | Post-surgical knee pain | 8 | 2 | 75% | 2 | 75% |
| 13 | Post-surgical back pain | 9 | 2 | 78% | 2 | 78% |
| 14 | Plantar fasciitis | 4 | 0 | 100% | 1 | 75% |
| 15 | Plantar fasciitis | 3 | 0 | 100% | 1 | 67% |
| 16 | Post-surgical knee pain | 7 | 0 | 100% | 1 | 86% |
| 17 | Acute lower back pain | 6 | 0 | 100% | 0 | 100% |
| 18 | Severe low back & leg pain | 10 | 2 | 80% | 3 | 70% |
| 19 | Shoulder pain & restriction | 4 | 0 | 100% | 0 | 100% |
| 20 | Post-surgical shoulder pain | 5 | 0 | 100% | 0 | 100% |
| 21 | Chronic shoulder pain | 5 | 0 | 100% | 0 | 100% |
| 22 | Acute upper back pain | 6 | 0 | 100% | 0 | 100% |
| 23 | Acute shoulder pain | 6 | 2 | 67% | 2 | 67% |
| 24 | Chronic shoulder pain | 9 | 1 | 89% | 3 | 67% |
| 25 | Neck & shoulder pain | 8 | 1 | 88% | 3 | 63% |
| 26 | Chronic headache/migraine | 6 | 0 | 100% | 0 | 100% |
| Mean | | 5.7 | 0.4 | 95% | 1 | 84% |

Again referring primarily to Table 2, the method of transdermally administering the particular embodiment of the inventive composition included: i) identifying the site of one or more symptoms, typically pain, and having the subject assess their perceived pain level on a scale ranging from 0 to 10, with 0 being the least amount of pain and 10 being the greatest amount of pain (indicated in column three as "Pre-Admin Pain Level"); ii) determining the cutaneous nerve branch(es) or main nerve trunk(s) liable for the one or more symptoms; iii) confirming the liability of the cutaneous nerve branch(es) or main nerve trunk(s) for the one or more symptoms by palpation; and iv) transdermally administering the inventive composition along the nerve pathway of the cutaneous nerve branch(es) or main nerve trunk(s) liable for the one or more symptoms, focusing on areas where the cutaneous nerve branch(es) or main nerve trunk(s) emerge superficially from deeper regions. Generally, the inventive composition was transdermally administered for a time period of about sixty seconds. Following, the subject reassessed their perceived pain level at about five minutes after the transdermal administration of the inventive composition (indicated in column four as "5 Minutes Post-Admin Pain Level") and again at about twenty-four hours after the transdermal administration of the inventive composition (indicated in column six as "24 Hours Post-Admin Pain Level").

Again referring primarily to Table 2, the mean pre-administration perceived pain level was 5.7/10 whereas the mean five minutes post-administration perceived pain level was 0.4/10, resulting in a mean 95% reduction in perceived pain level (each subject's percent reduction in perceived pain level indicated in column five as "Percent Reduction in Pain Level") in relation to the pre-administration perceived pain level. The mean twenty-four hour post-administration perceived pain level was 1/10, resulting in a mean 84% reduction in perceived pain level (each subject's percent reduction in perceived pain level indicated in column seven as "Percent Reduction in Pain Level") in relation to the pre-administration perceived pain level.

Now referring primarily to Table 3, which evidences the results of a method of transdermally administering a particular embodiment of the inventive composition to twelve subjects (indicated in column 1 as "Subject Number") who presented with various pain-related complaints (indicated in column 2 as "Primary Complaint"). As to this particular embodiment, the inventive composition included dextrose in an amount of about 20% by weight of the inventive composition, sodium bicarbonate in an amount of about 5% by weight of the inventive composition, and vehicle in an amount of about 75% by weight of the inventive composition.

TABLE 3

| Subject Number | Primary Complaint | Pre-Admin Pain Level | 1 Minute Post-Admin Pain Level | Percent Reduction in Pain Level |
| --- | --- | --- | --- | --- |
| 1 | Abdominal pain | 6 | 1 | 83% |
| 2 | Knee pain | 6 | 1 | 83% |
| 3 | Metacarpal-phalangeal joint pain | 6 | 0.5 | 92% |
| 4 | Carpal tunnel pain | 6 | 0 | 100% |
| 5 | Supraspinatus tendon pain | 10 | 2 | 80% |
| 6 | Wrist rheumatoid arthritis | 3 | 3 | 0% |
| 7 | Lower back pain | 9 | 3 | 67% |
| 8 | Foot complex regional pain syndrome | 3.4 | 1.5 | 56% |
| 9 | Knee pain | 5 | 0 | 100% |
| 10 | Achilles tendon pain | 6 | 1 | 83% |
| 11 | Wrist pain | 9 | 0 | 100% |
| 12 | Lower back pain | 7 | 1.5 | 79% |
|  | Mean | 6.4 | 1.2 | 77% |

Again referring primarily to Table 3, the method of transdermally administering the particular embodiment of the inventive composition included: i) identifying the site of one or more symptoms, typically pain, and having the subject assess their perceived pain level on a scale ranging from 0 to 10, with 0 being the least amount of pain and 10 being the greatest amount of pain (indicated in column three as "Pre-Admin Pain Level"); ii) determining the cutaneous nerve branch(es) or main nerve trunk(s) liable for the one or more symptoms; iii) confirming the liability of the cutaneous nerve branch(es) or main nerve trunk(s) for the one or more symptoms by palpation; and iv) transdermally administering the inventive composition along the nerve pathway of the cutaneous nerve branch(es) or main nerve trunk(s) liable for the one or more symptoms, focusing on areas where the cutaneous nerve branch(es) or main nerve trunk(s) emerge superficially from deeper regions. Generally, the inventive composition was transdermally administered for a time period of about sixty seconds. Following, the subject reassessed their perceived pain level at about one minute after the transdermal administration of the inventive composition (indicated in column four as "1 Minute Post-Admin Pain Level").

Again referring primarily to Table 3, the mean pre-administration perceived pain level was 6.4/10 whereas the mean one minute post-administration perceived pain level was 1.2/10, resulting in a mean 77% reduction in perceived pain level (each subject's percent reduction in perceived pain level indicated in column five as "Percent Reduction in Pain Level") relative to the pre-administration perceived pain level.

Now referring primarily to Table 4, which evidences the results of a method of transdermally administering a particular embodiment of the inventive composition to nine subjects (indicated in column 1 as "Subject Number") who presented with various pain-related complaints (indicated in column 2 as "Primary Complaint"). As to this particular embodiment, the inventive composition included dextrose in an amount of about 20% by weight of the inventive composition, sodium bicarbonate in an amount of about 5% by weight of the inventive composition, and vehicle in an amount of about 75% by weight of the inventive composition.

TABLE 4

| Subject Number | Primary Complaint | Pre-Admin Pain Level | 1 Minute Post-Admin Pain Level | Percent Reduction in Pain Level |
| --- | --- | --- | --- | --- |
| 1 | Neck pain | 6 | 1 | 83% |
| 2 | Plantar fasciitis | 6 | 0 | 100% |
| 3 | Carpal tunnel pain | 6 | 0 | 100% |
| 4 | Plantar fasciitis pain | 6 | 2 | 67% |
| 5 | Bilateral ankle pain | 4 | 0 | 100% |
| 6 | Carpal tunnel pain | 4 | 0 | 100% |
| 7 | Extensor ligament pain | 4 | 0 | 100% |
| 8 | Achilles tendon pain | 8 | 1 | 88% |
| 9 | Knee pain | 6 | 0 | 100% |
|  | Mean | 5.6 | 0.4 | 93% |

Again referring primarily to Table 4, the method of transdermally administering the particular embodiment of the inventive composition included: i) identifying the site of one or more symptoms, typically pain, and having the subject assess their perceived pain level on a scale ranging from 0 to 10, with 0 being the least amount of pain and 10 being the greatest amount of pain (indicated in column three as "Pre-Admin Pain Level"); ii) determining the cutaneous nerve branch(es) or main nerve trunk(s) liable for the one or more symptoms; iii) confirming the liability of the cutaneous nerve branch(es) or main nerve trunk(s) for the one or more symptoms by palpation; iv) transdermally administering the inventive composition along the nerve pathway of the cutaneous nerve branch(es) or main nerve trunk(s) liable for the one or more symptoms, focusing on areas where the cutaneous nerve branch(es) or main nerve trunk(s) emerge superficially from deeper regions; and v) administering ultrasound to enhance skin penetration of the inventive composition. Generally, the inventive composition was transdermally administered for a time period of about sixty seconds and ultrasound was administered for a time period of about five minutes. Following, the subject reassessed their perceived pain level at about one minute after the ultrasound administration (indicated in column four as "1 Minute Post-Admin Pain Level").

Again referring primarily to Table 4, the mean pre-administration perceived pain level was 5.6/10 whereas the mean one minute post-administration perceived pain level was 0.4/10, resulting in a mean 93% reduction in perceived pain level (each subject's percent reduction in perceived pain level indicated in column five as "Percent Reduction in Pain Level") relative to the pre-administration perceived pain level.

Now referring primarily to Table 5, which evidences the results of the transdermal administration of a particular embodiment of the inventive composition, a first compound, a second compound, and a third compound (as detailed in column one) to a subject who presented with lower back pain in four distinct regions (a first region, a second region, a third region, and a fourth region) along superior cluneal nerves, as detailed in column two. The inventive composition, first compound, second compound, and third compound were transdermally administered to the first, second, third, and fourth regions, respectively.

As to this particular embodiment, the inventive composition included dextrose in an amount of about 20% by weight of the inventive composition, sodium bicarbonate in an amount of about 5% by weight of the inventive composition, and vehicle in an amount of about 75% by weight of the inventive composition.

The first compound included dextrose in an amount of about 10% by weight of the first compound, tannic acid in an amount of about 2% by weight of the first compound, aloe vera in an amount of about 0.75% by weight of the first compound, and vehicle in an amount of about 87.25% by weight of the first compound.

The second compound included mannitol in an amount of about 20% by weight of the second compound and vehicle in an amount of about 80% by weight of the second compound.

The third compound included dextrose in an amount of about 20% by weight of the third compound and vehicle in an amount of about 80% by weight of the third compound.

third, and fourth regions of pain symptoms; ii) applying 2.5 kg/cm$^2$ of pressure via an algometer to each of the first, second, third, and fourth regions of pain symptoms and having the subject assess their perceived pain level on a scale ranging from 0 to 10, with 0 being the least amount of pain and 10 being the greatest amount of pain (indicated in column three as "Pre-Admin Pain Level"); iii) determining the cutaneous nerve branch(es) or main nerve trunk(s) liable for the pain symptoms in each of the first, second, third, and fourth regions; iv) confirming the liability of the cutaneous nerve branch(es) or main nerve trunk(s) for the pain symptoms in each of the first, second, third, and fourth regions by palpation; and v) transdermally administering the inventive composition along the nerve pathway liable for the pain symptoms proximate the first region; vi) transdermally administering the first compound along the nerve pathway liable for the pain symptoms proximate the second region; vii) transdermally administering the second compound along the nerve pathway liable for the pain symptoms proximate the third region; and viii) transdermally administering the third compound along the nerve pathway liable for the pain symptoms proximate the fourth region. Generally, the inventive composition and each of the first, second, and third compounds were transdermally administered for a time period of about sixty seconds. Following, 2.5 kg/cm$^2$ of pressure was applied via an algometer to each of the first, second, third, and fourth regions of pain symptoms at about five minutes after the transdermal administration and the subject reassessed their perceived pain level (indicated in column four as "5 Minutes Post-Admin Pain Level") and again at about fifteen minutes after the transdermal administration, 2.5 kg/cm$^2$ of pressure was applied via an algometer to each of the first, second, third, and fourth regions of pain symptoms and the subject reassessed their perceived pain level (indicated in column six as "15 Minutes Post-Admin Pain Level").

Again referring primarily to Table 5, regarding the inventive composition transdermally administered to the first region, the subject reported an 89% reduction in perceived pain level at five minutes post-administration (indicated in column five as "5 Minutes Post-Admin Pain Level") in relation to the pre-administration perceived pain level and an 89% reduction in perceived pain level at fifteen minutes post-administration (indicated in column five as "15 Minutes Post-Admin Pain Level") in relation to the pre-administration perceived pain level. Regarding the first compound transdermally administered to the second region, the subject reported a 50% reduction in perceived pain level at five

TABLE 5

| Inventive Composition and Compounds | Distinct Region | Pre-Admin Pain Level | 5 Minutes Post-Admin Pain Level | Precent Reduction in Pain Level | 15 Minutes Post-Admin Pain Level | Percent Reduction in Pain Level |
|---|---|---|---|---|---|---|
| Inventive Composition | First Region | 9 | 1 | 89% | 1 | 89% |
| First Compound | Second Region | 10 | 5 | 50% | 5 | 50% |
| Second Compound | Third Region | 9 | 4 | 56% | 3 | 66% |
| Third Compound | Fourth Region | 10 | 3 | 70% | 2 | 80% |

Again referring primarily to Table 5, the method of transdermally administering the particular embodiment of the inventive composition and each of the first, second, and third compounds included: i) identifying the first, second, minutes post-administration (indicated in column five as "5 Minutes Post-Admin Pain Level") in relation to the pre-administration perceived pain level and a 50% reduction in perceived pain level at fifteen minutes post-administration (indicated in column five as "15 Minutes Post-Admin Pain Level") in relation to the pre-administration perceived pain level. Regarding the third compound transdermally administered to the third region, the subject reported a 56% reduction in perceived pain level at five minutes post-administration (indicated in column five as "5 Minutes Post-Admin Pain Level") in relation to the pre-administra- The second compound included mannitol in an amount of about 20% by weight of the second compound and vehicle in an amount of about 80% by weight of the second compound.

The third compound included dextrose in an amount of about 20% by weight of the third compound and vehicle in an amount of about 80% by weight of the third compound.

TABLE 6

| Inventive Composition and Compounds | Distinct Region | Pre-Admin Pain Level | 5 Minutes Post-Admin Pain Level | Percent Reduction in Pain Level | 15 Minutes Post-Admin Pain Level | Percent Reduction in Pain Level |
|---|---|---|---|---|---|---|
| Inventive Composition | First Region | 10 | 1 | 90% | 0 | 100% |
| First Compound | Second Region | 8 | 4 | 50% | 4 | 50% |
| Second Compound | Third Region | 7 | 2 | 72% | 2 | 72% |
| Third Compound | Fourth Region | 7 | 1 | 86% | 1 | 86% | tion perceived pain level and a 66% reduction in perceived pain level at fifteen minutes post-administration (indicated in column five as "15 Minutes Post-Admin Pain Level") in relation to the pre-administration perceived pain level. Regarding the fourth compound transdermally administered to the fourth region, the subject reported a 70% reduction in perceived pain level at five minutes post-administration (indicated in column five as "5 Minutes Post-Admin Pain Level") in relation to the pre-administration perceived pain level and an 80% reduction in perceived pain level at fifteen minutes post-administration (indicated in column five as "15 Minutes Post-Admin Pain Level") in relation to the pre-administration perceived pain level. Overall, of the inventive composition, and first, second, and third compounds, the greatest percent reduction in perceived pain level at both five minutes post-administration and fifteen minutes post-administration was observed following transdermal administration of the inventive composition.

Now referring primarily to Table 6, which evidences the results of the transdermal administration of a particular embodiment of the inventive composition, the first compound, the second compound, and the third compound (as detailed in column one) to a subject who presented with knee pain in four distinct regions (a first region, a second region, a third region, and a fourth region) along cutaneous branches of the femoral nerve, as detailed in column two. Upon presentation, the subject was medicating with oxycodone/acetaminophen (5/325 milligrams every four to six hours), yet still reported significant perceived pain. The inventive composition, first compound, second compound, and third compound were transdermally administered to the first, second, third, and fourth regions, respectively.

As to this particular embodiment, the inventive composition included dextrose in an amount of about 20% by weight of the inventive composition, sodium bicarbonate in an amount of about 5% by weight of the inventive composition, and vehicle in an amount of about 75% by weight of the inventive composition.

The first compound included dextrose in an amount of about 10% by weight of the first compound, tannic acid in an amount of about 2% by weight of the first compound, aloe vera in an amount of about 0.75% by weight of the first compound, and vehicle in an amount of about 87.25% by weight of the first compound.

Again referring primarily to Table 6, the method of transdermally administering the particular embodiment of the inventive composition and each of the first, second, and third compounds included: i) identifying the first, second, third, and fourth regions of pain symptoms; ii) applying 2.5 kg/cm$^2$ of pressure via an algometer to each of the first, second, third, and fourth regions of pain symptoms and having the subject assess their perceived pain level on a scale ranging from 0 to 10, with 0 being the least amount of pain and 10 being the greatest amount of pain (indicated in column three as "Pre-Admin Pain Level"); iii) determining the cutaneous nerve branch(es) or main nerve trunk(s) liable for the pain symptoms in each of the first, second, third, and fourth regions; iv) confirming the liability of the cutaneous nerve branch(es) or main nerve trunk(s) for the pain symptoms in each of the first, second, third, and fourth regions by palpation; and v) transdermally administering the inventive composition along the nerve pathway liable for the pain symptoms proximate the first region; vi) transdermally administering the first compound along the nerve pathway liable for the pain symptoms proximate the second region; vii) transdermally administering the second compound along the nerve pathway liable for the pain symptoms proximate the third region; and viii) transdermally administering the third compound along the nerve pathway liable for the pain symptoms proximate the fourth region. Generally, the inventive composition and each of the first, second, and third compounds were transdermally administered for a time period of about sixty seconds. Following, 2.5 kg/cm$^2$ of pressure was applied via an algometer to each of the first, second, third, and fourth regions of pain symptoms at about five minutes after the transdermal administration and the subject reassessed their perceived pain level (indicated in column four as "5 Minutes Post-AdminPain Level") and again at about fifteen minutes after the transdermal administration, 2.5 kg/cm$^2$ of pressure was applied via an algometer to each of the first, second, third, and fourth regions of pain symptoms and the subject reassessed their perceived pain level (indicated in column six as "15 Minutes Post-Admin Pain Level").

Again referring primarily to Table 6, regarding the inventive composition transdermally administered to the first region, the subject reported a 90% reduction in perceived pain level at five minutes post-administration (indicated in column five as "5 Minutes Post-Admin Pain Level") in relation to the pre-administration perceived pain level and a 100% reduction in perceived pain level at fifteen minutes post-administration (indicated in column five as "15 Minutes Post-Admin Pain Level") in relation to the pre-administration perceived pain level. Regarding the first compound transdermally administered to the second region, the subject reported a 50% reduction in perceived pain level at five minutes post-administration (indicated in column five as "5 Minutes Post-Admin Pain Level") in relation to the pre-administration perceived pain level and a 50% reduction in perceived pain level at fifteen minutes post-administration (indicated in column five as "15 Minutes Post-Admin Pain Level") in relation to the pre-administration perceived pain level. Regarding the third compound transdermally administered to the third region, the subject reported a 72% reduction in perceived pain level at five minutes post-administration (indicated in column five as "5 Minutes Post-Admin Pain Level") in relation to the pre-administration perceived pain level and a 72% reduction in perceived pain level at fifteen minutes post-administration (indicated in column five as "15 Minutes Post-Admin Pain Level") in relation to the pre-administration perceived pain level. Regarding the fourth compound transdermally administered to the fourth region, the subject reported an 86% reduction the second inventive composition, the first compound, and the second compound were transdermally administered to the first, second, third, and fourth regions, respectively.

As to this particular embodiment, the first inventive composition included dextrose in an amount of about 25% by weight of the first inventive composition, sodium bicarbonate in an amount of about 2.5% by weight of the first inventive composition, and vehicle in an amount of about 72.5% by weight of the first inventive composition.

The second inventive composition included dextrose in an amount of about 20% by weight of the second inventive composition, sodium bicarbonate in an amount of about 10% by weight of the second inventive composition, and vehicle in an amount of about 70% by weight of the second inventive composition.

The first compound included sodium bicarbonate in an amount of about 2.5% by weight of the first compound and vehicle in an amount of about 97.5% by weight of the first compound.

The second compound included mannitol in an amount of about 2.5% by weight of the second compound and vehicle in an amount of about 97.5% by weight of the second compound.

TABLE 7

| Inventive Composition and Compounds | Distinct Region | Pre-Admin Pain Level | 5 Minutes Post-Admin Pain Level | Percent Reduction in Pain Level | 15 Minutes Post-Admin Pain Level | Percent Reduction in Pain Level |
| --- | --- | --- | --- | --- | --- | --- |
| First Inventive Composition | First Region | 7 | 3 | 57% | 3 | 57% |
| Second Inventive Composition | Second Region | 6 | 1 | 83% | 1 | 83% |
| First Compound | Third Region | 9 | 8 | 11% | 7 | 22% |
| Second Compound | Fourth Region | 6 | 3 | 50% | 3 | 50% | in perceived pain level at five minutes post-administration (indicated in column five as "5 Minutes Post-Admin Pain Level") in relation to the pre-administration perceived pain level and an 86% reduction in perceived pain level at fifteen minutes post-administration (indicated in column five as "15 Minutes Post-Admin Pain Level") in relation to the pre-administration perceived pain level. Overall, of the inventive composition, and first, second, and third compounds, the greatest percent reduction in perceived pain level at both five minutes post-administration and fifteen minutes post-administration was observed following transdermal administration of the inventive composition.

Now referring primarily to Table 7, which evidences the results of the transdermal administration of a first inventive composition, a second inventive composition, a first compound, and a second compound (as detailed in column one) to a subject who presented with lower back pain in four distinct regions (a first region, a second region, a third region, and a fourth region), as detailed in column two. Upon presentation, the subject was having a trochanteric shot administered every four weeks. In addition, the subject was medicating with a steroid pak, celecoxib (200 milligrams every twenty-four hours), and oxycodone/acetaminophen (10/325 milligrams every four hours), yet still reported significant perceived pain. The first inventive composition, Again referring primarily to Table 7, the method of transdermally administering the particular embodiment of the inventive composition and each of the first, second, and third compounds included: i) identifying the first, second, third, and fourth regions of pain symptoms; ii) applying 2.0 $kg/cm^2$ of pressure via an algometer to each of the first, second, third, and fourth regions of pain symptoms and having the subject assess their perceived pain level on a scale ranging from 0 to 10, with 0 being the least amount of pain and 10 being the greatest amount of pain (indicated in column three as "Pre-Admin Pain Level"); iii) determining the cutaneous nerve branch(es) or main nerve trunk(s) liable for the pain symptoms in each of the first, second, third, and fourth regions; iv) confirming the liability of the cutaneous nerve branch(es) or main nerve trunk(s) for the pain symptoms in each of the first, second, third, and fourth regions by palpation; and v) transdermally administering the inventive composition along the nerve pathway liable for the pain symptoms proximate the first region; vi) transdermally administering the first compound along the nerve pathway liable for the pain symptoms proximate the second region; vii) transdermally administering the second compound along the nerve pathway liable for the pain symptoms proximate the third region; and viii) transdermally administering the third compound along the nerve pathway liable for the pain symptoms proximate the fourth region. Generally, each of the first inventive composition, the second inventive composition, the first compound, and the second compound were transdermally administered for a time period of about sixty seconds. Following, 2.5 kg/cm$^2$ of pressure was applied via an algometer to each of the first, second, third, and fourth regions of pain symptoms at about five minutes after the transdermal administration and the subject reassessed their perceived pain level (indicated in column four as "5 Minutes Post-Admin Pain Level") and again at about fifteen minutes after the transdermal administration, 2.5 kg/cm$^2$ of pressure was applied via an algometer to each of the first, second, third, and fourth regions of pain symptoms and the subject reassessed their perceived pain level (indicated in column six as "15 Minutes Post-Admin Pain Level").

Again referring primarily to Table 7, regarding the first inventive composition transdermally administered to the first region, the subject reported a 57% reduction in perceived pain level at five minutes post-administration (indicated in column five as "5 Minutes Post-Admin Pain Level") in relation to the pre-administration perceived pain level and a 57% reduction in perceived pain level at fifteen minutes post-administration (indicated in column five as "15 Minutes Post-Admin Pain Level") in relation to the pre-administration perceived pain level. Regarding the second inventive composition transdermally administered to the second region, the subject reported an 83% reduction in perceived pain level at five minutes post-administration (indicated in column five as "5 Minutes Post-Admin Pain Level") in relation to the pre-administration perceived pain level and an 83% reduction in perceived pain level at fifteen minutes post-administration (indicated in column five as "15 Minutes Post-Admin Pain Level") in relation to the pre-administration perceived pain level. Regarding the first compound transdermally administered to the third region, the subject reported an 11% reduction in perceived pain level at five minutes post-administration (indicated in column five as "5 Minutes Post-Admin Pain Level") in relation to the pre-administration perceived pain level and a 22% reduction in perceived pain level at fifteen minutes post-administration (indicated in column five as "15 Minutes Post-AdminPain Level") in relation to the pre-administration perceived pain level. Regarding the second compound transdermally administered to the fourth region, the subject reported a 50% reduction in perceived pain level at five minutes post-administration (indicated in column five as "5 Minutes Post-Admin Pain Level") in relation to the pre-administration perceived pain level and a 50% reduction in perceived pain level at fifteen minutes post-administration (indicated in column five as "15 Minutes Post-Admin Pain Level") in relation to the pre-administration perceived pain level. Overall, of the first inventive composition, the second inventive composition, the first compound, and the second compound, the greater percent reduction in perceived pain level at both five minutes post-administration and fifteen minutes post-administration was observed following transdermal administration of the first and second inventive compositions, with the greatest percent reduction in perceived pain level at both five minutes post-administration and fifteen minutes post-administration observed following transdermal administration of the second inventive composition.

A method of producing a particular embodiment of the inventive composition can include combining an amount of sugar or sugar alcohol, an amount of alkalizing agent, and an amount of vehicle; and formulating the inventive composition for transdermal administration.

As used herein, the term "combination or combining" refers to any method of putting two or more materials together. Such methods include, but are not limited to, mixing, blending, commingling, concocting, homogenizing, ultrasonic homogenizing, incorporating, intermingling, fusing, joining, shuffling, stirring, coalescing, integrating, confounding, joining, uniting, creating a stable suspension of two immiscible liquids via any number of means such as emulsions, or the like.

As to particular embodiments, the method of producing a particular embodiment of the inventive composition can include combining the sugar or sugar alcohol, alkalizing agent, and vehicle, whereby each can be combined in an amount as described above.

As to particular embodiments, the method of producing a particular embodiment of the inventive composition can further include combining one or more additional components to formulate the inventive composition, whereby the one or more additional components can be as described above or can be other additional components.

As can be easily understood from the foregoing, the basic concepts of the present invention may be embodied in a variety of ways. The invention involves numerous and varied embodiments of a pain relieving system and methods for making and using such pain relieving systems including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "combination" should be understood to encompass disclosure of the act of "combining"—whether explicitly discussed or not—and, conversely, were there effectively disclosure of the act of "combining", such a disclosure should be understood to encompass disclosure of a "combination" and even a "means for combining". Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the pain relieving systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method for relieving pain, comprising:
   transdermally administering a composition along a nerve pathway of a nerve, said composition comprising pain relievers consisting of:
   (i) an amount of mannitol between 5% to 30% by weight of said composition; and
   (ii) an amount of sodium bicarbonate between 5% to 15% by weight of said composition;
   wherein transdermal administration of said composition is effective to decrease neurogenic pain associated with said nerve.

2. The method of claim 1, wherein said transdermal administration of said composition is effective to decrease neurogenic inflammation.

3. The method of claim 1, further comprising transdermally administering said composition formulated as a fluid selected from the group consisting of: lotion, cream, emulsion, ointment, gel, foam, paste, oil, lipid delivery system, spray, and drops.

4. The method of claim 1, further comprising administering one or more physical skin penetration enhancement techniques before, during, or after transdermally administering said composition.

5. The method of claim 4, wherein said skin penetration enhancement techniques are selected from the group consisting of: phonophoresis, sonophoresis, iontophoresis, electroporation, radiofrequency-driven skin microchanneling, microneedles, massage, occlusion, heating, and cooling.

6. The method of claim 1, further comprising transdermally administering said composition to alkalize a perineural environment proximate a nerve.

7. The method of claim 6, wherein alkalization of said perineural environment comprises adjusting a pH of said perineural environment from a lesser alkalinity toward a greater alkalinity.

8. The method of claim 1, further comprising transdermally administering said composition to decrease an amount of hydrogen ions in a perineural environment proximate said nerve.

9. The method of claim 1, further comprising transdermally administering said composition to decrease a viscosity of hyaluronic acid.

10. The method of claim 9, wherein a decrease in said viscosity of said hyaluronic acid decreases mechanical irritation of said nerve by fascia enveloping said nerve.

11. The method of claim 1, wherein said amount of mannitol is between 20% to 30% by weight of said composition.

12. The method of claim 1, wherein said amount of mannitol is between 10% to 30% by weight of said composition.

13. The method of claim 1, wherein said amount of sodium bicarbonate is between 10% to 15% by weight of said composition.

* * * * *